US011833356B2

(12) United States Patent
Lu et al.

(10) Patent No.: US 11,833,356 B2
(45) Date of Patent: Dec. 5, 2023

(54) EXTRANEURAL CUFF WITH FLEXIBLE INTERCONNECTS FOR STIMULATION AND RECORDING

(71) Applicant: GALVANI BIOELECTRONICS LIMITED, Middlesex (GB)

(72) Inventors: Bo Lu, Mountain View, CA (US); Brian Marc Pepin, Mountain View, CA (US)

(73) Assignee: GALVANI BIOELECTRONICS LIMITED, Middlesex (GB)

( * ) Notice: Subject to any disclaimer, the term of this patent is extended or adjusted under 35 U.S.C. 154(b) by 288 days.

(21) Appl. No.: 15/999,524

(22) PCT Filed: Feb. 17, 2017

(86) PCT No.: PCT/US2017/018368
§ 371 (c)(1),
(2) Date: Aug. 17, 2018

(87) PCT Pub. No.: WO2017/143189
PCT Pub. Date: Aug. 24, 2017

(65) Prior Publication Data
US 2021/0205622 A1 Jul. 8, 2021

Related U.S. Application Data

(60) Provisional application No. 62/296,277, filed on Feb. 17, 2016.

(51) Int. Cl.
*A61N 1/36* (2006.01)
*A61N 1/05* (2006.01)
*A61N 1/372* (2006.01)

(52) U.S. Cl.
CPC ....... *A61N 1/36135* (2013.01); *A61N 1/0556* (2013.01); *A61N 1/0558* (2013.01); *A61N 1/37229* (2013.01)

(58) Field of Classification Search
CPC .............. A61N 1/36135; A61N 1/0556; A61N 1/0558; A61N 1/37229
See application file for complete search history.

(56) References Cited

U.S. PATENT DOCUMENTS 6,292,703 B1 * 9/2001 Meier .................... A61B 5/287
607/118
2003/0040785 A1 * 2/2003 Maschino ............ A61N 1/0556
607/118
(Continued)

FOREIGN PATENT DOCUMENTS

WO WO 2003/082080 A2 10/2003
WO WO 2011/084450 A1 7/2011
(Continued)

OTHER PUBLICATIONS

Article Fabrication of implantable microelectrode arrays by laser cutting of silicone rubber and platinum foil to M Schuettler et al. 2005 J. Neural Eng. 2 S121 (Year: 2005).*
(Continued)

*Primary Examiner* — Paula J Stice
(74) *Attorney, Agent, or Firm* — Merchant & Gould P.C.

(57) ABSTRACT

An electrode system for neuromodulation and for recording of signals indicative of nerve activity is provided. The system can include a plurality of electrodes provided on a flexible, non-conductive substrate. The substrate can be rolled into a cuff for encircling a nerve bundle of a patient. The plurality of electrodes on the cuff can be interconnected using flexible conductors provided on the substrate. In one implementation, the electrodes can be interconnected using conductors that have spring-like configuration. Flexibility of the conductors allows the cuff to expand and contract with the nerve without causing excessive stress/strain at the nerve-cuff interface.

14 Claims, 5 Drawing Sheets

(56) References Cited

U.S. PATENT DOCUMENTS

| | | | | |
|---|---|---|---|---|
| 2004/0220651 | A1* | 11/2004 | Kuzma | A61N 1/0541 |
| | | | | 607/125 |
| 2007/0233204 | A1* | 10/2007 | Lima | A61N 1/0551 |
| | | | | 607/46 |
| 2009/0259265 | A1* | 10/2009 | Stevenson | H05K 3/321 |
| | | | | 607/2 |
| 2013/0333918 | A1* | 12/2013 | Lotfi | B23K 26/364 |
| | | | | 174/121 R |
| 2015/0174396 | A1* | 6/2015 | Fisher | A61N 1/3605 |
| | | | | 600/377 |
| 2016/0331326 | A1* | 11/2016 | Xiang | A61B 5/24 |

FOREIGN PATENT DOCUMENTS

| | | | |
|---|---|---|---|
| WO | WO 2013/149181 | A1 | 10/2013 |
| WO | WO 2015/080991 | A1 | 6/2015 |

OTHER PUBLICATIONS

Meacham, K., Giuly, R. J., Guo, L., Hochman, S., & DeWeerth, S. P. (2008). A lithographically-patterned, elastic multi-electrode array for surface stimulation of the spinal cord. Biomedical Microdevices, 10(2), 259-269. https://doi.org/10.1007/s10544-007-9132-9 . (Year: 2008).*

International Patent Application No. PCT/US2017/018368; Int'l Written Opinion and the Search Report; dated May 12, 2017; 9 pages.

* cited by examiner

EXTRANEURAL CUFF WITH FLEXIBLE INTERCONNECTS FOR STIMULATION AND RECORDING

RELATED APPLICATIONS

This application is a U.S. national application of International Application No. PCT/US17/18368, filed Feb. 17, 2017, which claims priority to U.S. Provisional Application No. 62/296,277, filed Feb. 17, 2016, which is incorporated herein by reference in the entirety.

BACKGROUND

Technical Field

The present disclosure relates generally to neuromodulation, and more particularly, to an electrode system for providing electrical stimulation to nerves and for acquiring signals indicative of nerve activity.

Background Description

Neuromodulation relates to the modulation of nerve activity by delivering electrical pulses or pharmaceutical agents directly to a target neural tissue. Neuromodulation holds promise for treating or improving a number of physiological conditions, for example, depression, urinary incontinence, heart failure conditions, chronic pain, Parkinson's disease, etc. In particular, electrical stimulation of different types of neural tissue can provide treatment for a number of different physiological disorders, for example, deep brain stimulation (DBS) to treat Parkinson's disease, sacral nerve stimulation to treat pelvic disorders and incontinence, spinal cord stimulation to treat ischemic disorders, and vagus nerve stimulation to treat epilepsy, chronic depression, inflammation resulting from arthritis or Crohn's disease, etc.

Extraneural cuff electrode systems are commonly used for electrical stimulation and/or recording of signals indicative of nerve activity. Traditional cuff electrode systems generally include a single planar electrode or a plurality of planar electrodes fabricated on a non-conductive substrate. The substrate is manually wrapped around a target nerve bundle in the form of a cuff or a sleeve to place the electrode(s) in contact with the nerve bundle. To maintain intimate contact between the nerve and the electrode(s), the cuff has to be wrapped snugly around the nerve bundle, which may induce mechanical stresses on the nerve and cause pain and/or damage to the nerve. Cuff electrodes tend to cause nerve trauma particularly when the nerve swells due to physiological changes.

To prevent nerve damage, the substrate may be formed of a soft or flexible material to accommodate swelling of the nerve. However, the presence of conductors, wires, or other electronic circuitry on the cuff may inhibit the cuff from loosening or expanding to accommodate swelling of the nerve. This problem may be more significant in case of multi-electrode cuffs which may have a lot of rigid interconnects.

Another solution to the problem of nerve trauma is to use a spiral nerve cuff, which is biased to self-wrap around a target nerve bundle and possesses a self-sizing property. As the nerve swells and contracts, the spiral cuff may expand and relax with the nerve, and thereby limit pain and nerve damage. However, the position of the electrodes relative to the nerve may change over time as the cuff expands and relaxes. Moreover, the manufacturing processes used to induce residual stress in the spiral cuff may have variability, which may make the self-curling of the cuff difficult to control.

Thus, there remains a need to develop an improved cuff electrode system for neuromodulation and for recording of signals indicative of nerve activity that limits or prevents nerve damage.

SUMMARY

The present disclosure is directed to an electrode system that can be place around a biological tissue, e.g., a nerve bundle. The electrode system can be wrapped around the biological tissue to provide electrical stimulation to the tissue and/or to acquire electrical biosignals from the tissue (e.g., nerve activity from a nerve bundle). The acquired biosignals can be spontaneous signals generated by the tissue and/or evoked signals generated in response to applied stimulation.

One aspect of the present disclosure is a device for neuromodulation. The device comprises a flexible, non-conductive substrate arranged in the form of a cuff for placement around a nerve bundle, and a plurality of electrodes that are provided on the substrate. The plurality of electrodes are interconnected by flexible conductors fabricated on the substrate.

Another aspect of the present disclosure is directed to a method of fabricating an electrode system for neuromodulation. The method may include applying a first polymer layer to a first carrier wafer and depositing, electroplating, and etching a seed layer onto the first polymer layer to form electrical conductors in a serpentine pattern. The method may also include applying a second polymer layer onto the first polymer layer and electrical conductors, wherein the second polymer layer forms contact vias connected to the electrical conductors. The method may further include patterning electrodes over portions of the electrical conductors, wherein the contact vias connect the electrodes to the electrical conductors. The method may also include etching the first and second polymer layers to form a serpentine pattern. The method may further include releasing the first carrier wafer from the underside of the electrode system, and attaching to the opposing side of the electrode system a second carrier wafer coated with a crystal bond layer. The method may also include coating a substrate to the underside of the electrode system and releasing the second carrier wafer and cleaning a surface of the electrode system released from the second carrier wafer.

Other embodiments of this disclosure are contained in the accompanying drawings, description, and claims. Thus, this summary is exemplary only, and is not to be considered restrictive.

BRIEF DESCRIPTION OF DRAWINGS

The accompanying drawings, which are incorporated in and constitute a part of this specification, illustrate the disclosed embodiments and together with the description, serve to explain the principles of the various aspects of the disclosed embodiments. The accompanying drawings are schematics and not necessarily drawn to scale. In the drawings.

It is to be understood that both the foregoing general description and the following detailed description are exemplary and explanatory only and are not restrictive of the disclosed embodiments, as claimed.

DETAILED DESCRIPTION OF EXEMPLARY EMBODIMENTS

Reference will now be made to certain embodiments consistent with the present disclosure, examples of which are illustrated in the accompanying drawings. Wherever possible, the same reference numbers are used throughout the drawings to refer to the same or like parts.

The present disclosure describes an electrode system for electrical stimulation of a target tissue and/or for acquiring electrical signals from a target tissue. The electrode system comprises a substrate that can be wrapped around a length of the target tissue in the form of a cuff or sleeve. The target tissue can be a nerve bundle, muscle fiber, or any other tissue that can be encircled by the substrate of the electrode system. Although the present disclosure is described with reference to a nerve bundle, a person of ordinary skill in the art would understand that the electrode system of the present disclosure can be used with any biological tissue that can be electrically stimulated and/or tissue from which electrical signals can be acquired.

Neuromodulation as described herein may be defined as electrical stimulation of nerve fibers or nerve tissue for triggering, amplifying, inhibiting or blocking propagation of action potentials along nerve fibers. The electrical stimulation may be carried out by transmitting of electrical pulses along the nerve fiber, as described herein.

Figure 1:
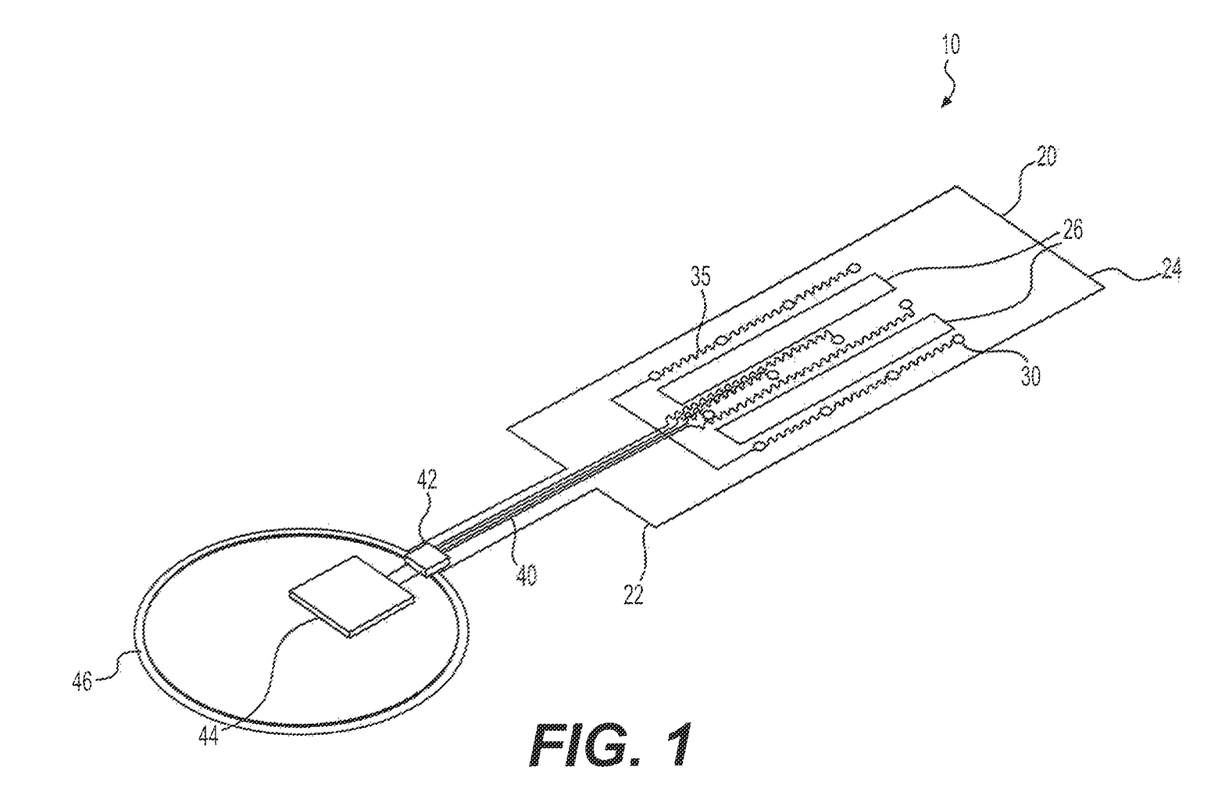
FIG. 1 is a schematic top view of an electrode system, according to an exemplary embodiment.
Figure 2:
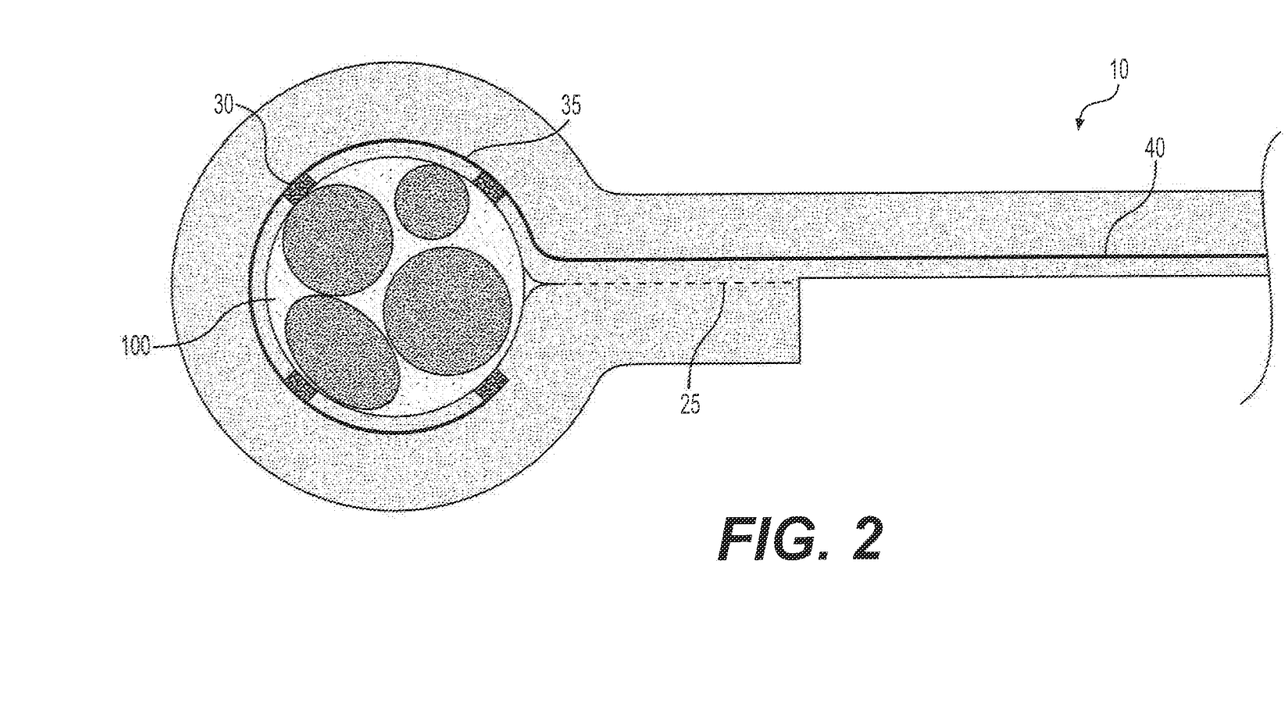
FIG. 2 is a schematic of an implanted electrode system, according to an exemplary embodiment.

FIG. 1 shows a top view of an electrode system 10 in accordance with exemplary embodiments of the present disclosure. Electrode system 10 can comprise a substrate 20 that can be wrapped around a nerve bundle 100, as shown in FIG. 2. Substrate 20 can be formed of a flexible, non-conductive material. Use of a flexible material can allow substrate 20 to expand and contract as necessary to accommodate swelling of the nerve following implantation of electrode system 10, and thereby prevent nerve damage and trauma. In exemplary embodiments, substrate 20 can be made of silicone. In some embodiments, substrate 20 is not a continuous sheet and can include cut-outs 26 to accommodate swelling and/or growth of the target nerve and formation of scar tissue around the implantation site.

In exemplary embodiments, substrate 20 can be wrapped snugly around nerve bundle 100 to establish close contact between the one or more electrodes provided on substrate 20 and nerve bundle 100. In some embodiments, substrate 20 can be wrapped completely around nerve bundle 100 in the form of a sleeve. In such embodiments, lateral edges 22 and 24 of substrate 20 can be sutured onto each other to avoid possible displacement of electrode system 10 following implantation. In some embodiments, lateral edge 22 and/or lateral edge 24 can include tabs 25 that can be connected together to secure electrode system 10 on nerve bundle 100. In some embodiments, one of the lateral edges 22, 24 may be connected via tab 25 to the body of substrate 20, as shown in FIG. 2. In another embodiment, substrate 20 can be wrapped partially around nerve bundle 100 in the form of a half-cuff. In such embodiments, lateral edges 22 and 24 do not contact each other when substrate 20 is wrapped around nerve bundle 20.

Electrode system 10 can comprise a plurality of electrodes 30 fabricated on substrate 20, as shown in FIG. 1. The plurality of electrodes 30 can be used to provide electrical stimulation to the nerve and/or to sense nerve activity of the nerve. The number of electrodes 30 can vary based on the application and/or the length of the target nerve fiber. For example, the number of electrodes 30 can range from two to about 100 or more. In exemplary embodiments, one or more sets of three electrodes 30 each can be provided on substrate 20. In such embodiments, a stimulation electrode can be flanked on opposite sides by two ground electrodes. In some embodiments, four sets of three electrodes 30 each can be provided on substrate 20.

In exemplary embodiments, electrodes 30 can be connected by conductive interconnects to an electronic controller. Component of an exemplary controller are depicted in FIG. 1. The components depicted in FIG. 1 are exemplary only, and are not to be considered restrictive. The controller can be positioned in close proximity to electrode system 10 within or on the patient's body. In some embodiments, the controller can be provided on substrate 20 of electrode system 10. In another embodiment, the controller can be implanted in the patient body near electrode system 10. In yet another embodiment, the controller can be a wearable device.

In exemplary embodiments, the controller can be a stand-alone platform equipped with wireless power and communication capability. In some embodiments, the controller can have an energy storage device 44 that can be charged wirelessly. Energy storage device 44 can include a supercapacitor, a battery, or some other type of charging system that can be charged wirelessly by a remote processing device placed outside the patient's body. The controller can also include one or more antenna coils 46 for reception of wireless power. In some embodiments, optical powering using an array of photovoltaic cells can be used to power the embedded electronics of the controller or to recharge its battery.

In exemplary embodiments, the controller can receive signals indicative of the nerve activity from electrodes 30, which the controller can transmit either wirelessly or through a wired connection to the remote processing device for processing, analysis and/or storage. In other embodiments, the controller can receive electrical stimulation parameters wirelessly or through a wired connection from the remote processing device and the controller can apply stimulation pulses to the nerve fiber via electrodes 30 based on the received stimulation parameters. In such embodiments, the controller can include electronic circuitry 42 to generate the stimulation pulses. In case of wireless communication to and from the controller, the controller can include one or more antennas, transceivers, and other electronics for enabling wireless communication. For example, in some embodiments, antenna coils 46 can be used for radio frequency communication with the remote processing device.

In exemplary embodiments, the controller can have a microprocessor to process and/or analyze the signals indicative of nerve activity sensed by electrodes 30. In some embodiment, the controller can adaptively adjust electrical stimulation parameters in real-time based on sensed responses. The electrical stimulation parameters may include for example, the timing of the electrical pulses (e.g., at what time of day the pulses are emitted), the duration of the pulses (e.g., one minute, five minutes, ten minutes, etc.), the amplitude or intensity of the pulses, the electrodes 30 used to generate the pulses (e.g., to specify a particular direction and/or orientation of the pulse), the waveform of the pulses (e.g., the width or wavelength of the pulses, the shape of the pulses, etc.), and/or any other suitable parameter of the pulse consistent with the disclosed embodiments.

In some embodiments, the controller can have on-chip electronics to pre-process the signals indicative of the nerve activity prior to transmitting the signals to the remote processing device. In such embodiments, the controller can include amplifiers, analog-to-digital converters, multiplexers, and other electronic circuitry to pre-process the signals.

In exemplary embodiments, electrodes 30 provided on substrate 20 can be interconnected by electrical conductors 35 fabricated on substrate 20. In some embodiments, conductors 35 can lead to conductors 40 provided at the periphery of substrate 20. In such embodiments, conductors 35 can be provided at the site of electrodes 30, while conductors 40 can be provided at the margins of substrate 20 where electrodes 30 are not present, as shown in FIGS. 1 and 2. Conductors 40 can connect conductors 35 to the controller. Conductors 35 and 40 may be defined as flexible interconnections made substantially out of a conductive material designed to allow electricity to flow between electronic components (e.g., electrodes 30 and the controller). Thus, electrodes 30 are operatively coupled to the controller via conductors 35 and 40. In some embodiments, conductors 35 and 40 can be comparable, such that conductors 35 connect electrodes 30 all the way to the controller.

In exemplary embodiments, conductors 35 provided on a planar surface of substrate 20 can be flexible. In some embodiments, conductors 35 can be stretchable so that when substrate 20 expands in response to swelling of the nerve, conductors 35 can flex concomitantly to accommodate the expansion of substrate 20. In exemplary embodiments, conductors 35 can also return or contract to its original shape and dimension when substrate 20 contracts in response to de-swelling of the nerve. That is, in some embodiments, conductors 35 can be elastic. In exemplary embodiments, conductors 35 can be microfabricated into a mechanical spring. In some embodiments, conductors 35 can be microfabricated into an undulating, meandering, springy, or wave-shaped line on substrate 20, as shown in FIG. 1. The undulating pattern of conductors 35 should not be considered restrictive of the invention. Conductors 35 can have any shape, pattern, or configuration that allows conductors 35 to be flexible in nature. Thus, in exemplary embodiments, conductors 35 can allow substrate 20 to expand and relax with nerve bundle 100 without introducing stress/strain at the nerve-cuff interface. In such embodiments, substrate 20 can be sutured to itself when wrapped around nerve bundle 100 (as illustrated in FIG. 2) without inhibiting the expansion and contraction of nerve bundle 100.

In exemplary embodiments, conductors 35 can have minimum feature sizes that are smaller than that of traditional conductors having straight-line geometry. In some embodiment, conductors 35 can have microscale dimensions. For example, in some embodiments, conductors 35 can have width of about 10 µm to about 100 µm. In some embodiments, conductors 35 can have width of less than 10 µm. In some embodiments, conductors 35 can have width of about 1 µm. In some embodiments, conductors 35 can have width of less than 1 µm. In exemplary embodiments, conductors 35 can have height of about 100 nm to about 10 µm.

In exemplary embodiments, conductors 35 can be made of a conductive material. For example, in one embodiment, conductors 35 can include titanium. In another embodiment, conductors 35 can include platinum or platinum-iridium alloy. In yet another embodiment, conductors 35 can include gold.

Conductors 35 can be microfabricated on a planar surface of substrate 20 in a variety of different ways. In some embodiments, conductors 35 can be microfabricated using contact lithography. In another embodiment, conductors 35 can be deposited on substrate 20 using physical vapor deposition (e.g., sputtering) techniques. In another embodiment, conductors 20 can be stamped or laminated onto substrate 20. In yet another embodiment, conductors 35 can be etched out of a larger straight interconnect line using precision laser ablation with a short wavelength laser.

Figure 3A:
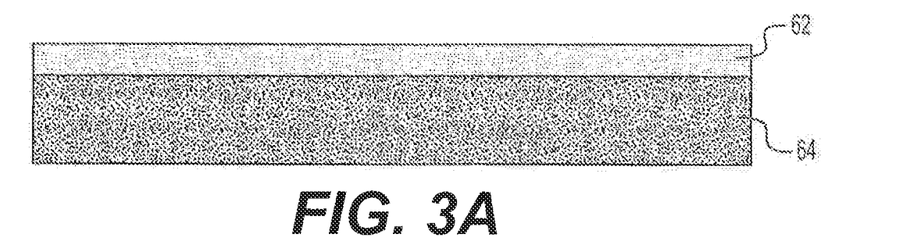
FIGS. 3A-3H illustrate cross-sectional views of a microfabrication process for manufacturing electrode systems, according to exemplary embodiments.
Figure 3B:
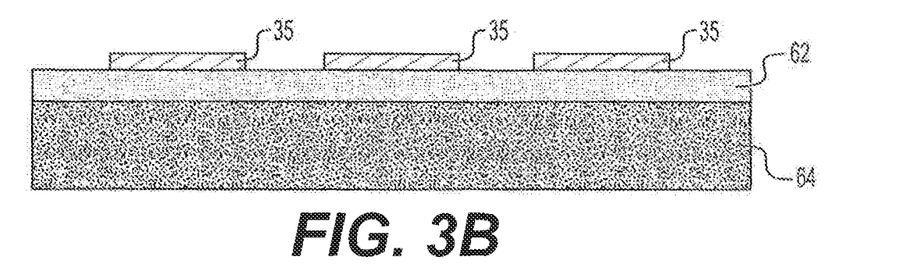
Figure 3C:
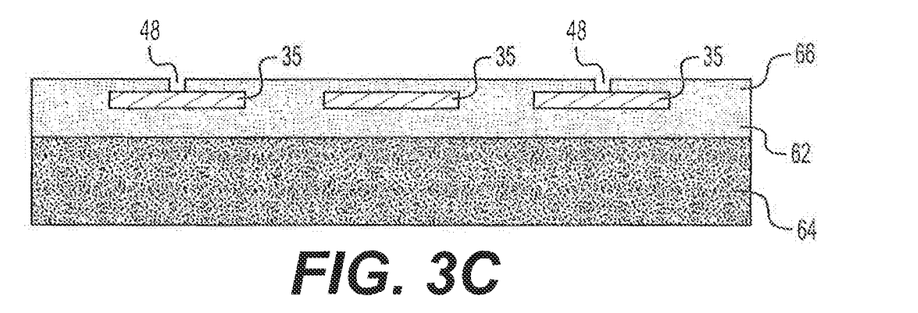
Figure 3D:
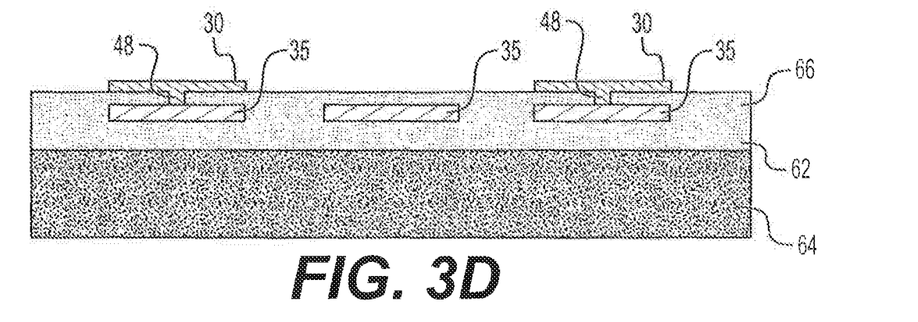

FIGS. 3A-3H illustrate cross-sectional views of a microfabrication process for manufacturing electrode systems, as described herein. The process may begin with applying a first polymer layer 62 to a carrier wafer 64, as shown in FIG. 3A. First polymer layer 62 and carrier wafer 64 may be formed of any suitable material. For example, first polymer layer 62 may be formed of polyimide, liquid crystal polymer (LCP), paraylene, or other flexible polymer material. Carrier wafer 64 may be formed of silicone. In some embodiments, the thickness of first polymer layer 62 may be about 6.5 µm. The process may then include depositing, electroplating, and etching a seed layer 66 to form electrical conductors 35, as shown in FIG. 3B. Electrical conductors 35 may be formed of any suitable material or combination of materials, including for example, gold (AU), chromium (Cr) and gold (Au). In some embodiments, the thickness of electrical conductors 35 may be about 3 µm. The process may then include applying a second polymer layer 66 that forms contact vias 48, as shown in FIG. 3C. Lithography and resist may be used to etch contact vias 48. In some embodiments, second polymer layer 66 may be formed of the same material or a different material as first polymer layer 62 and may have the same thickness or a different thickness. The process may then include patterning electrodes 30 above portions of electrical conductors 35, as shown in FIG. 3D. Electrodes 30 may be patterned using suitable lithography and lift-off methods. Electrodes 30 may be formed of any suitable material or combination of materials, including for example, titanium (Ti) and platinum (Pt), platinum iridium (PtIr), titanium nitride (TiN), and iridium oxide (IrOx).

Figure 3E:
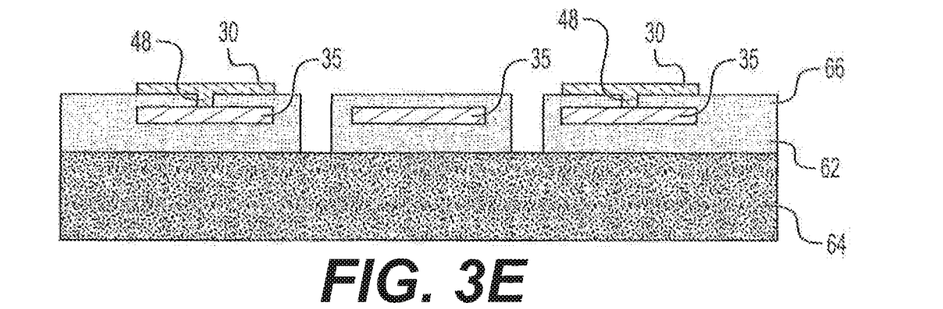
Figure 3F:
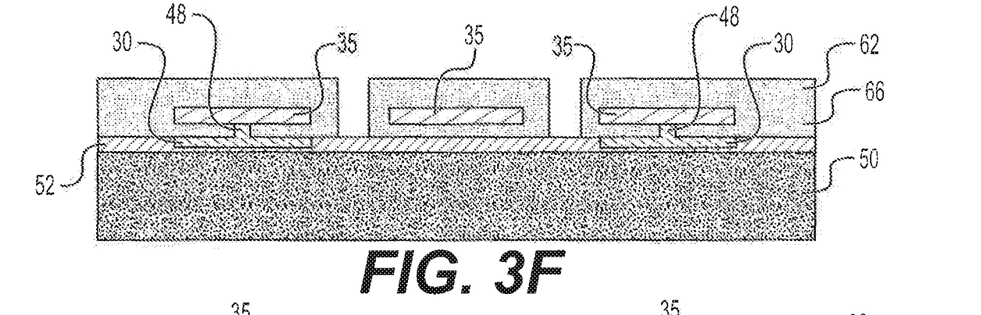
Figure 3G:
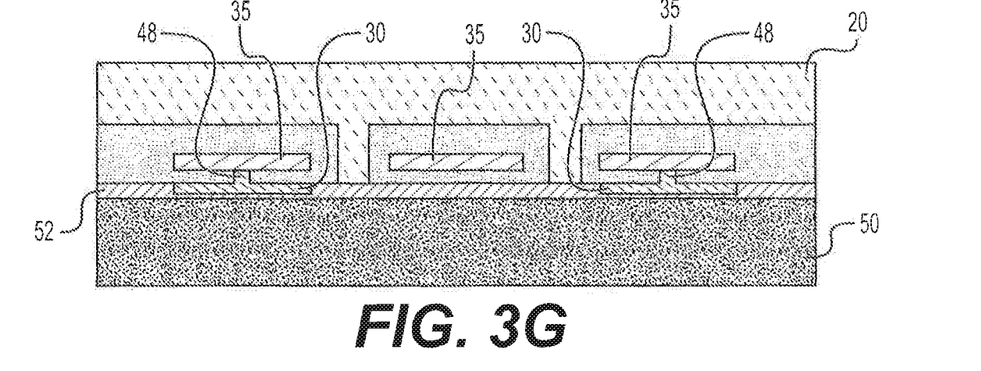
Figure 3H:
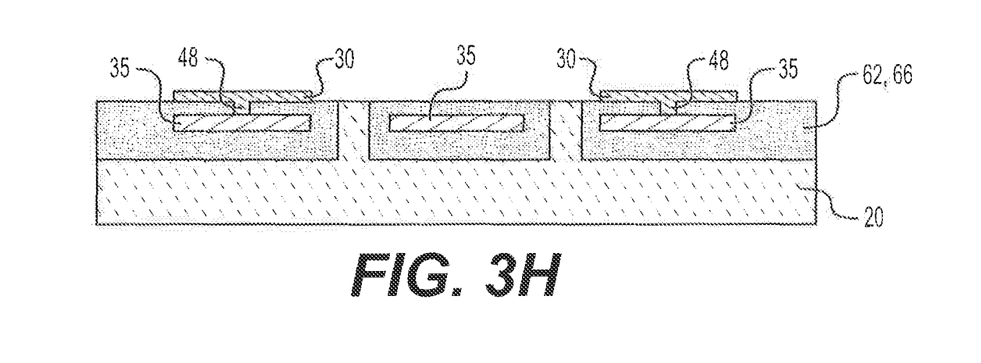

As shown in FIG. 3E, the process may then include etching the first and second polymer layers 62, 66. First and second polymer layers 62, 66 may be etched using any suitable methods, including for example, lithography and a resist. First and second polymer layers 62, 66 may be etched to form a variety of patterns, including for example, a serpentine pattern as will be discussed further herein. The process may then include releasing carrier wafer 64 from the underside of the electrode system assembly, flipping over the electrode system, and attaching to the opposing side of the electrode system a carrier wafer 50 coated with a crystal bond layer 52, as shown in FIG. 3F. The process may then include applying a coating to from substrate 20 on the underside of the electrode system, as shown in FIG. 3G. Substrate 20 may be formed of any suitable material, including for example, silicone. In some embodiments, the thickness of substrate 20 may be, for example, about 300 µm. The process may then include releasing the electrode system assembly from crystal bond 52, as shown in FIG. 3H. The process may include cleaning the released surface with acetone and isopropyl alcohol (IPA).

Figure 4:
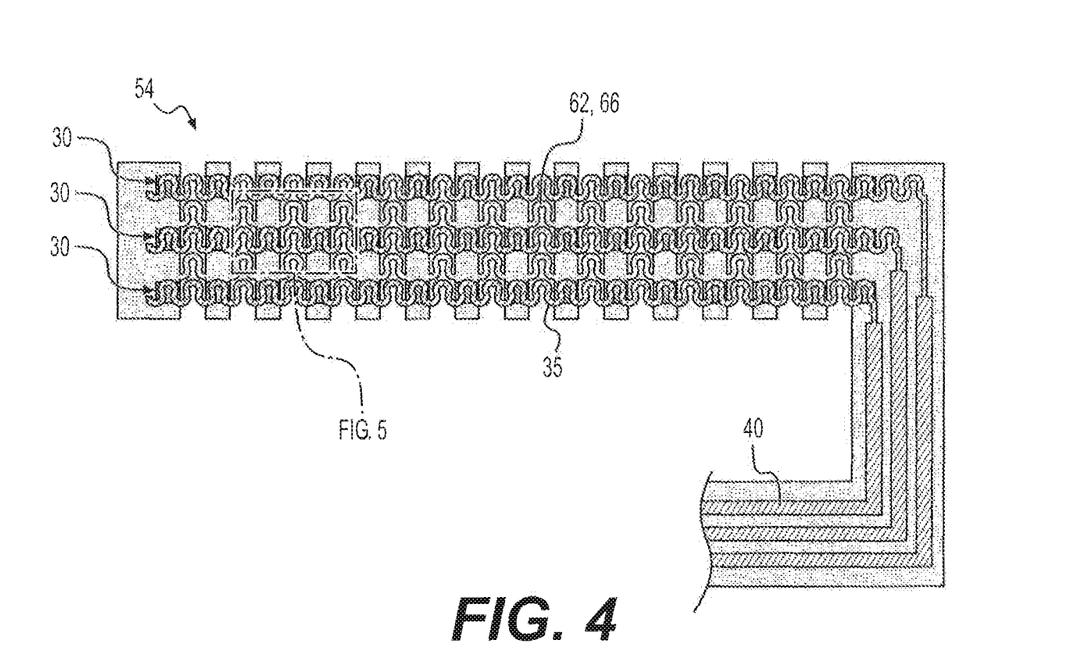
FIG. 4 is a schematic top view of an electrode system, according to an exemplary embodiment.
Figure 5:
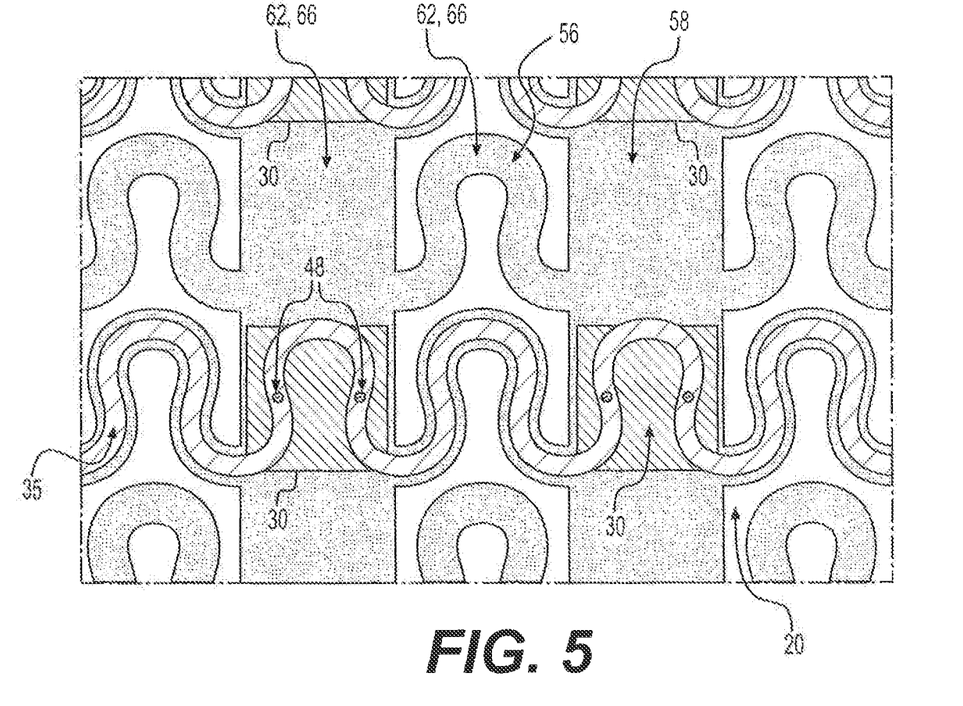
FIG. 5 is an enlarged schematic top view of a portion of the electrode system of FIG. 4.

FIG. 4 is a schematic top view of an electrode system 54, according to an exemplary embodiment. FIG. 5 is an enlarged schematic of a portion of 54 electrode system of FIG. 4. As illustrated in FIGS. 4 and 5, electrical conductors 35 may be manufactured to form a curvilinear or serpentine pattern. Similarly, portions of first and second polymer layers 62, 66 may also be manufactured to from a serpentine spring pattern. For example, as illustrated in FIG. 5, first and second polymer layers 62, 66 may be etched to form a staggered pattern where spring sections 56 are separated by solid sections 58. The serpentine patterns can function like a spring increasing the stretching ability of electrode system 54. The serpentine patterns can enable electrode system 54 to withstand large in-plane elongation without breaking. For example, one an electrode system 54 was cycled 1000 times to an elongation of 40% without damage or impedance increase. The substrate 20 applied to the backside can also increase the robustness an durability of electrode system 54.

Electrical conductors 35, as described herein, may be electroplated to reduce the impedance. In some embodiments, the impedance between the end of conductors 40 and an electrode 30 at the far end of electrode system 54 may be about 6 ohms or less. As shown in FIG. 5, each electrode 30 may have two contact vias 48 connecting the electrode to electrical conductors 35.

In exemplary embodiments, antenna coils 46 can be flexible or compliant, so that antenna coils 46 do not constrain or obstruct the expansion and contraction of substrate 20 when the controller is provided on substrate 20 or in close proximity to substrate 20. Flexibility of antenna coils 46 can also improve movement and compliance of muscles at the site of implantation.

The foregoing description has been presented for purposes of illustration. It is not exhaustive and is not limited to the precise forms or embodiments disclosed. Modifications and adaptations will be apparent to those skilled in the art from consideration of the specification and practice of the disclosed embodiment. Moreover, while illustrative embodiments have been described herein, the disclosure includes the scope of any and all embodiments having equivalent elements, modifications, omissions, combinations (e.g., of aspects across various embodiments), adaptations and/or alterations as would be appreciated by those skilled in the art based on the present disclosure. The limitations in the claims are to be interpreted broadly based on the language employed in the claims and not limited to examples described in the present specification or during the prosecution of the application. The examples are to be construed as non-exclusive. Furthermore, the steps of the disclosed methods can be modified in any manner, including by reordering steps and/or inserting or deleting steps. It is intended, therefore, that the specification and examples be considered as illustrative only, with a true scope and spirit being indicated by the following claims and their full scope of equivalents.

The invention claimed is:

1. A device for neuromodulation, the device comprising:
 a flexible, non-conductive substrate arranged in a form of a cuff for placement around a nerve bundle; and
 a plurality of electrodes provided on the substrate, wherein the plurality of electrodes are interconnected by flexible electrical conductors fabricated on a planar surface of the substrate, and wherein the flexible electrical conductors are arranged over portions of the plurality of electrodes and are patterned to increase the flexibility of the flexible electrical conductors and connect each electrode of the plurality of electrodes to the electrical conductors.

2. The device of claim 1, wherein the substrate has at least two opposing edges, and, in use, the two opposing edges are sutured to each other to secure the cuff on the nerve bundle.

3. The device of claim 1, further comprising a controller operatively coupled to the plurality of electrodes, wherein the controller is configured to control the operation of the plurality of electrodes and enable wireless communication, wherein the controller is configured to wirelessly receive one or more electrical stimulation parameters and transmit signals indicative of nerve activity, wherein the plurality of electrodes are configured to detect the nerve activity.

4. The device of claim 3, wherein the controller is located on the substrate.

5. The device of claim 3, wherein the controller comprises a plurality of flexible antenna coils.

6. The device of claim 1, wherein the electrical conductors have a height of between 100 nm and 10 μm.

7. The device of claim 1, wherein the electrical conductors have a width of between 10 μm and 100 μm.

8. The device of claim 1, wherein the substrate comprises silicone.

9. The device of claim 1, wherein the conductors are made of platinum.

10. The device of claim 1, wherein the conductors are made of gold.

11. The device of claim 1, wherein the conductors are made of platinum iridium alloy.

12. The device of claim 1, wherein the conductors are made of titanium.

13. The device of claim 1, wherein the conductors are elastic.

14. The device of claim 1, wherein the conductors are stretchable.

* * * * *

UNITED STATES PATENT AND TRADEMARK OFFICE
CERTIFICATE OF CORRECTION

| | | |
|---|---|---|
| PATENT NO. | : 11,833,356 B2 | Page 1 of 1 |
| APPLICATION NO. | : 15/999524 | |
| DATED | : December 5, 2023 | |
| INVENTOR(S) | : Lu et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 779 days.

Signed and Sealed this
First Day of July, 2025

Coke Morgan Stewart
*Acting Director of the United States Patent and Trademark Office*